(12) United States Patent
Chadwick et al.

(10) Patent No.: US 11,497,900 B2
(45) Date of Patent: Nov. 15, 2022

(54) ENHANCED FLUID DELIVERY SYSTEM

(71) Applicant: Allurion Technologies, Inc., Natick, MA (US)

(72) Inventors: Samuel Chadwick, Newton, MA (US); David W. Nelson, Wayland, MA (US); Andy Elder, Roxbury, MA (US); Matthew S. Lake, Laguna Niguel, CA (US); Bruce A. Horwitz, Newton, MA (US)

(73) Assignee: Allurion Technologies, Inc., Natick, MA (US)

( * ) Notice: Subject to any disclaimer, the term of this patent is extended or adjusted under 35 U.S.C. 154(b) by 350 days.

(21) Appl. No.: 16/713,583

(22) Filed: Dec. 13, 2019

(65) Prior Publication Data

US 2020/0188644 A1 Jun. 18, 2020

Related U.S. Application Data

(60) Provisional application No. 62/779,158, filed on Dec. 13, 2018.

(51) Int. Cl.
*A61M 25/10* (2013.01)
*A61F 5/00* (2006.01)
*A61M 25/00* (2006.01)

(52) U.S. Cl.
CPC ....... *A61M 25/10181* (2013.11); *A61F 5/003* (2013.01); *A61M 2025/0098* (2013.01)

(58) Field of Classification Search
CPC .......... A61M 25/0014; A61M 25/0052; A61M 25/0053; A61M 25/0054; A61M 25/0074; A61M 25/01; A61M 25/0102; A61M 25/0105; A61M 25/10; A61M 25/1018; A61M 25/10181; A61M 25/1025; A61M 2025/0059; A61M 2025/006; A61M 2025/0098; A61M 2025/1054; A61F 5/003; A61F 5/0036; A61F 5/0043; A61F 5/0089; A61B 17/12131; A61B 17/12136; B29L 2031/7542; B29L 2031/7543; Y10S 128/06; Y10S 128/26
See application file for complete search history.

(56) References Cited

U.S. PATENT DOCUMENTS

| 2,911,988 A | 11/1959 | Ravn |
| 3,586,018 A | 6/1971 | Bogardh et al. |
| 3,638,733 A | 2/1972 | De Rouville et al. |
| 3,853,116 A | 12/1974 | Bucalo |
| 4,133,315 A | 1/1979 | Berman et al. |

(Continued)

FOREIGN PATENT DOCUMENTS

| CA | 2925648 | 5/2007 |
| CA | 2865056 | 8/2013 |

(Continued)

OTHER PUBLICATIONS

Stony Brook Medicine "Obalon Swallowable Balloon Capsules" Feb. 21, 2017, 2 pages. Retrieved from the Internet [Sep. 2, 2020] URL: https://www.youtube.com/watch?v=CEznWcGacLl.

*Primary Examiner* — Robert A Lynch
(74) *Attorney, Agent, or Firm* — Levine Bagade Han LLP

(57) ABSTRACT

Methods and devices related to fluid delivery catheters and more particularly relates to catheters used to deliver fluid to medical devices and/or position medical devices.

20 Claims, 9 Drawing Sheets

(56) References Cited

U.S. PATENT DOCUMENTS

| | | | |
|---|---|---|---|
| 4,141,771 A | 2/1979 | Barker et al. | |
| 4,370,374 A | 1/1983 | Raabe et al. | |
| 4,614,188 A * | 9/1986 | Bazell | A61M 25/10 604/920 |
| 4,723,547 A * | 2/1988 | Kullas | A61F 5/0036 604/909 |
| 4,732,188 A | 3/1988 | Gabrlik et al. | |
| 4,739,758 A | 4/1988 | Lai et al. | |
| 4,842,007 A | 6/1989 | Kurtz | |
| 4,899,747 A | 2/1990 | Garren et al. | |
| 4,949,756 A | 8/1990 | Melinyshyn et al. | |
| 5,018,665 A | 5/1991 | Sulmone | |
| 5,092,847 A * | 3/1992 | Pozzo | A61M 25/0102 600/585 |
| 5,181,921 A | 1/1993 | Makita et al. | |
| 5,222,970 A * | 6/1993 | Reeves | A61B 17/12109 604/164.05 |
| 5,336,123 A | 8/1994 | Laske et al. | |
| 5,348,537 A | 9/1994 | Wiesner et al. | |
| 5,496,203 A | 3/1996 | Murray | |
| 5,507,808 A | 4/1996 | Becker | |
| 5,595,521 A | 1/1997 | Becker | |
| 5,950,624 A | 9/1999 | Hart | |
| 6,162,251 A | 12/2000 | Kredovski | |
| 6,259,953 B1 | 7/2001 | Lucchesi et al. | |
| 6,367,499 B1 | 4/2002 | Taku | |
| 6,375,972 B1 | 4/2002 | Guo et al. | |
| 6,460,541 B1 | 10/2002 | Shah et al. | |
| 6,644,336 B2 | 11/2003 | Dolan | |
| 6,712,832 B2 | 3/2004 | Shah | |
| 6,814,097 B2 | 11/2004 | Girouard | |
| 6,939,292 B2 | 9/2005 | Mizuno et al. | |
| 7,172,613 B2 | 2/2007 | Wazne | |
| 7,485,093 B2 | 2/2009 | Glukhovsky | |
| 7,854,745 B2 | 12/2010 | Brister et al. | |
| 8,183,227 B1 | 5/2012 | Perrin et al. | |
| 8,202,291 B1 | 6/2012 | Brister et al. | |
| 8,287,562 B2 | 10/2012 | Kasic, II | |
| 8,292,911 B2 | 10/2012 | Brister et al. | |
| 8,585,676 B2 | 11/2013 | Shah | |
| 8,740,845 B2 | 6/2014 | Shah et al. | |
| 8,784,486 B2 | 7/2014 | Schuessler | |
| 8,814,898 B2 | 8/2014 | Gaur et al. | |
| 8,870,907 B2 | 10/2014 | Gaur et al. | |
| 8,974,483 B2 | 3/2015 | Gaur et al. | |
| 9,387,107 B2 | 7/2016 | Gaur et al. | |
| 9,463,106 B2 | 10/2016 | Khieu et al. | |
| 9,662,239 B2 | 5/2017 | Brister et al. | |
| 9,827,128 B2 | 11/2017 | Brister et al. | |
| 9,827,129 B2 | 11/2017 | Gaur et al. | |
| 9,849,018 B2 | 12/2017 | Wecker et al. | |
| 10,182,932 B2 | 1/2019 | Moss et al. | |
| 10,238,516 B1 | 3/2019 | Singh et al. | |
| 10,307,279 B2 | 6/2019 | Wecker et al. | |
| 10,470,908 B2 | 11/2019 | Nelson et al. | |
| 10,583,024 B2 | 3/2020 | Nelson et al. | |
| 10,588,768 B2 | 3/2020 | Nelson et al. | |
| 10,729,572 B2 | 8/2020 | Moss et al. | |
| 10,786,379 B2 | 9/2020 | Gaur et al. | |
| 11,098,813 B2 | 8/2021 | Nelson | |
| 2001/0018929 A1 | 9/2001 | Taku | |
| 2002/0183777 A1 | 12/2002 | Shannon | |
| 2002/0198470 A1 | 12/2002 | Imran et al. | |
| 2003/0106583 A1 | 6/2003 | Weng | |
| 2003/0171768 A1 | 9/2003 | McGhan | |
| 2003/0229263 A1 | 12/2003 | Connors et al. | |
| 2003/0229384 A1 | 12/2003 | Mon | |
| 2004/0044353 A1 | 3/2004 | Gannoe | |
| 2004/0073249 A1 * | 4/2004 | Trotta | A61M 25/0043 606/191 |
| 2004/0101540 A1 | 5/2004 | Cooker | |
| 2004/0146559 A1 | 7/2004 | Sowden et al. | |
| 2004/0186502 A1 | 9/2004 | Sampson et al. | |
| 2005/0055039 A1 | 3/2005 | Burnett et al. | |
| 2005/0096750 A1 | 5/2005 | Kagan et al. | |
| 2005/0150548 A1 | 7/2005 | Kita et al. | |
| 2006/0004323 A1 * | 1/2006 | Chang | A61F 2/186 604/28 |
| 2006/0222705 A1 | 10/2006 | Flanner et al. | |
| 2007/0010791 A1 | 1/2007 | Drechsler et al. | |
| 2007/0078476 A1 | 4/2007 | Hull et al. | |
| 2007/0250094 A1 | 10/2007 | Makower et al. | |
| 2008/0195226 A1 | 8/2008 | Williams et al. | |
| 2008/0241094 A1 | 10/2008 | Burnett et al. | |
| 2008/0243071 A1 | 10/2008 | Quijano et al. | |
| 2008/0249635 A1 | 10/2008 | Weitzner et al. | |
| 2008/0269555 A1 | 10/2008 | Paganon et al. | |
| 2008/0276992 A1 | 11/2008 | Nomichi et al. | |
| 2008/0306441 A1 * | 12/2008 | Brown | A61M 25/10 604/99.01 |
| 2009/0024227 A1 | 1/2009 | Lesh | |
| 2009/0048684 A1 | 2/2009 | Lesh | |
| 2009/0118756 A1 | 5/2009 | Valencon | |
| 2009/0192535 A1 | 7/2009 | Kasic | |
| 2009/0259246 A1 | 10/2009 | Eskaros et al. | |
| 2009/0275919 A1 * | 11/2009 | Todd | A61M 25/0102 604/509 |
| 2009/0277515 A1 | 11/2009 | Pechtold | |
| 2009/0299327 A1 | 12/2009 | Tilson et al. | |
| 2010/0062057 A1 | 3/2010 | Berge et al. | |
| 2010/0100116 A1 | 4/2010 | Brister et al. | |
| 2010/0114311 A1 | 5/2010 | Becker | |
| 2010/0121224 A1 | 5/2010 | Toyota et al. | |
| 2010/0137897 A1 | 6/2010 | Brister et al. | |
| 2010/0168511 A1 * | 7/2010 | Muni | A61M 25/0152 600/104 |
| 2010/0174307 A1 | 7/2010 | Birk | |
| 2010/0193050 A1 | 8/2010 | Job | |
| 2010/0246165 A1 | 9/2010 | Diaz et al. | |
| 2010/0274194 A1 | 10/2010 | Sobelman et al. | |
| 2011/0004236 A1 | 1/2011 | Priplata et al. | |
| 2011/0112383 A1 | 5/2011 | Voss et al. | |
| 2012/0141544 A1 | 6/2012 | Fuisz et al. | |
| 2012/0141545 A1 | 6/2012 | Fuisz et al. | |
| 2012/0232576 A1 | 9/2012 | Brister et al. | |
| 2012/0273050 A1 | 11/2012 | Metzger et al. | |
| 2013/0035711 A1 | 2/2013 | Schwab et al. | |
| 2013/0165873 A1 | 6/2013 | Morriss et al. | |
| 2013/0190796 A1 | 7/2013 | Tilson et al. | |
| 2013/0218190 A1 | 8/2013 | Gaur et al. | |
| 2013/0267984 A1 | 10/2013 | Gaur et al. | |
| 2013/0289604 A1 | 10/2013 | Brister et al. | |
| 2013/0296751 A1 | 11/2013 | Martin et al. | |
| 2014/0012363 A1 * | 1/2014 | Franano | A61B 17/12131 164/47 |
| 2014/0066967 A1 | 3/2014 | Levy et al. | |
| 2014/0180252 A1 * | 6/2014 | Gabriel | A61B 17/3415 604/99.04 |
| 2014/0188151 A1 | 7/2014 | Gaur et al. | |
| 2014/0296903 A1 | 10/2014 | Gaur et al. | |
| 2015/0196408 A1 | 7/2015 | Moss et al. | |
| 2016/0010758 A1 | 1/2016 | Nomichi et al. | |
| 2016/0045719 A1 * | 2/2016 | Ha | A61M 25/0023 606/196 |
| 2016/0109029 A1 | 4/2016 | Dulin | |
| 2016/0278957 A1 | 9/2016 | Gaur et al. | |
| 2017/0211715 A1 | 7/2017 | Balmaceda et al. | |
| 2017/0312111 A1 | 11/2017 | Sharma et al. | |
| 2018/0042747 A1 | 2/2018 | Gaur et al. | |
| 2018/0071127 A1 | 3/2018 | Wecker et al. | |
| 2018/0236203 A1 * | 8/2018 | Franklin | A61M 25/1002 |
| 2018/0311484 A1 | 11/2018 | Lake et al. | |
| 2018/0344498 A1 | 12/2018 | Moss et al. | |
| 2019/0076152 A1 * | 3/2019 | Franklin | A61B 17/12109 |
| 2019/0262157 A1 | 8/2019 | Nelson et al. | |
| 2019/0388258 A1 | 12/2019 | Nelson et al. | |
| 2019/0388259 A1 | 12/2019 | Nelson et al. | |
| 2020/0011442 A1 | 1/2020 | Nelson | |

(56) References Cited

U.S. PATENT DOCUMENTS

2020/0155335 A1    5/2020  Nelson et al.
2021/0341069 A1   11/2021  Nelson

FOREIGN PATENT DOCUMENTS

| | | |
|---|---|---|
| CN | 1387418 | 12/2002 |
| CN | 101384231 | 3/2009 |
| CN | 201977967 | 9/2011 |
| EP | 2139439 | 1/2010 |
| EP | 2817062 | 12/2014 |
| EP | 3117865 | 1/2017 |
| JP | 2008-513132 | 5/2008 |
| JP | 2008-515464 | 5/2008 |
| JP | 2010-523280 | 7/2010 |
| JP | 2011-517611 | 6/2011 |
| WO | WO 2000/012167 | 3/2000 |
| WO | WO 2006/020929 | 2/2006 |
| WO | WO 2009/059802 | 5/2009 |
| WO | WO 2009/059803 | 5/2009 |
| WO | WO 2011/106157 | 9/2011 |
| WO | WO 2013/126593 | 8/2013 |
| WO | WO 2014/074625 | 5/2014 |
| WO | WO 2015/066545 | 5/2015 |
| WO | WO 2016/145076 | 9/2016 |
| WO | WO 2017/136840 | 8/2017 |
| WO | WO 2018/142761 | 8/2018 |
| WO | WO 2019/165449 | 8/2019 |
| WO | WO 2020/010359 | 1/2020 |
| WO | WO 2020/123916 | 6/2020 |

\* cited by examiner

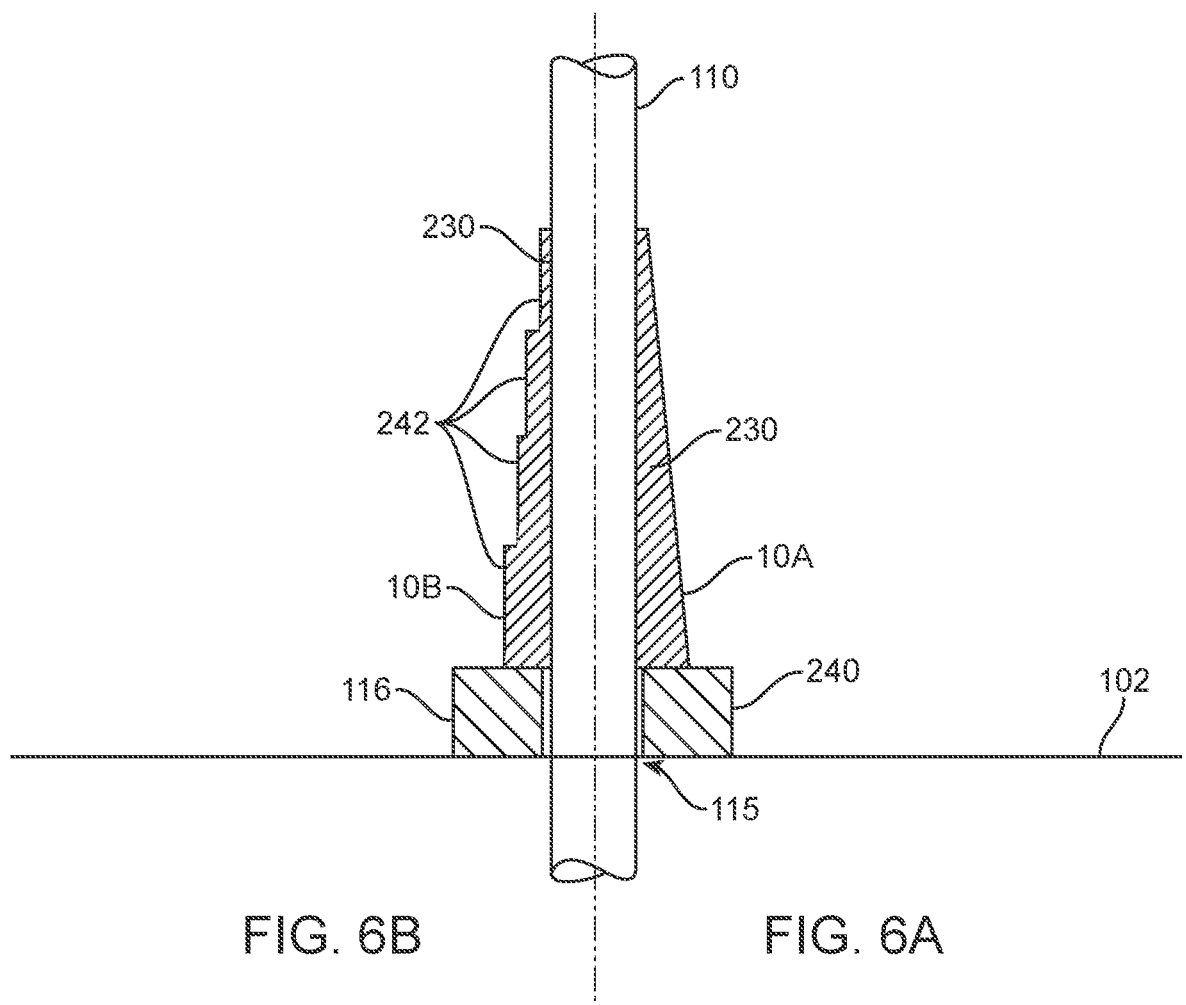

| Mass at which kinking observed | | |
|---|---|---|
| Trial Number | Strain Relieved | Un-relieved |
| 1 | 6.5213 | 2.9959 |
| 2 | 8.5259 | 2.9939 |
| 3 | 6.8107 | 2.4946 |
| 4 | 6.7128 | 2.9995 |
| 5 | 6.6243 | 2.4954 |
| 6 | 6.9476 | 2.4952 |
| Ave | 7.0238 | 2.7458 |
| STDEV | 0.7505 | 0.2746 |

FIG. 8

ENHANCED FLUID DELIVERY SYSTEM

CROSS-REFERENCE TO RELATED APPLICATIONS

This application claims benefit of U.S. Provisional Application No. 62/779,158 filed on Dec. 13, 2018, the entirety of which is incorporated by reference. This application is also related to PCT Application Number PCT/US2019/066185 filed Dec. 13, 2019, the entirety of which is incorporated by reference herein.

BACKGROUND OF THE INVENTION

The present invention generally relates to the field of fluid delivery catheters and more particularly relates to catheters used to deliver fluid to medical devices.

In medicine, a catheter is a thin tube made from medical grade materials serving a broad range of functions. Catheters are medical devices that facilitate the transfer of a fluid into or out of the body. Such catheters can be inserted into the body or remain external to the body. The fluid delivered by such catheters may be liquid or gaseous. By modifying the materials or adjusting the manufacturing process, it is possible to tailor catheters for cardiovascular, urological, gastrointestinal, neurovascular, and ophthalmic applications. In most applications the end of the catheter disposed inside the body is open-ended, with the open end positioned within the space or bodily part to or from which fluid is to be transferred.

In one variation, a catheter is used to fill and/or empty a balloon-like medical device. In such applications, the catheter can be closed-ended; that is, the fluid delivery end is pre-inserted in the medical device. For example, angioplasty is performed by inserting a deflated balloon attached to a catheter (a "balloon catheter") into the narrowed vessel. Then, the operator inflates the balloon to a fixed size. The expanding balloon dilates the constriction and blood vessel, allowing for improved blood flow through the vessel. The operator then deflates the balloon and withdraws the balloon catheter from the body. A second catheter balloon-filling application is the inflation of breast implants while a third application is the inflation of gastric balloons that occupy space in a patient's stomach.

In many situations a relatively stiff probe guides the catheter and/or attached medical device to its intended location. Open ended catheters can be positioned with a guide wire probe (see https://www.dicardiology.com/article/basics-guide-wire-technology), which can be inserted prior to the catheter, with the catheter advanced to the intended location for fluid delivery over the guide wire. Closed-end systems are also generally guided to the fluid delivery location with the help of a probe. Typically, these probes, which push the end of the device end of the catheter into position, are called stylets. Once the device is in location, the stylet is typically withdrawn from the catheter. http://www-.bostonscientific.com/en-US/products/guidewires.htm.

A major difference between open-ended catheters and catheters attached to medical devices is that the latter are generally constrained to enter the device at a fixed angle relative to the entrance port or opening in the device. Because of this constraint, the catheter is subject to pinching or kinking if the device rotates or moves relative to the catheter axis, reducing or cutting off the flow of fluid to the device.

In some instances, the entrance port of the medical device can include a strain relief component that modulates the constraint and eliminates, or greatly reduces, the possibility of catheter pinching or kinking. However, these solutions have drawbacks with some indwelling medical devices where the strain relief component causes irritation of tissue surrounding the device.

Another issue with stylets and guide wires involves the risk of physical damage if a thin, stiff probe inadvertently pushes against soft tissue. Guide wires are generally fabricated with flexible tips to help prevent such damage and to make it easier to direct the wire around corners. Stylets, on the other hand, may or may not have a flexible tip when the tip of the stylet is intended to push the catheter and attached device. Used in this mode, the flexible tip on a stylet may fold and become jammed in the catheter.

Thus, there remains a need for an improved catheter configuration that addresses the problems above. For example, such an improved catheter includes, but is not limited to, an angular strain relief approach that is compatible with non-rigid medical devices such as balloons and/or that must be non-irritating to a patient's organs when the catheter is removed from an in-dwelling medical device. There also remains a need for an angular strain relief approach for configurations where a flexible tube passes through a rigid interface. There also remains a need for a stylet that is stiff enough to push a medical device into position but that has a flexible tip to prevent the narrow stylet from pushing through and either damaging the attached medical device or injuring the patient.

SUMMARY OF THE INVENTION

The present invention relates to fluid delivery systems comprising catheters and to systems comprising catheters and stylets. Also disclosed herein are methods and devices for eliminating the angular strain on the catheters that lead to kinking and pinching. Methods and devices are also disclosed for reducing the risk to a device being pushed by a stylet and reducing the risk to a patient from a stiff-tipped stylet. In particular, a variation of the improved fluid delivery systems described herein include systems for filling medical devices where the device remains in the body after removal of the associated catheter from the device and the body. Variations of the systems and devices also include delivery systems having self-strain-relieving properties and having increased safety; for example, catheters that do not leave behind a potentially problematic strain-relief device on or in the medical device and stylets that have controlled stiffness tips.

The present disclosure includes medical devices and/or fluid delivery systems that are useful in certain medical procedures. For example, such a variation can include a medical device for positioning in a patient. In one example, this medical device includes a reservoir enclosed in the medical device and configured to receive a fluid; a catheter comprising a fill end and a delivery end, wherein the delivery end is configured to be fluidly coupled to the reservoir; a strain relief member supporting a portion of a length of the catheter at the delivery end, where the strain relief member increases a stiffness of the length to reduce kinking at the length when a force is applied on the catheter that deflects the catheter relative to the medical device; a stylet configured to fit within a lumen of the catheter; a stylet tip located at a far portion of the stylet, wherein a flexibility of the stylet tip is greater than a remainder of the stylet such that the stylet tip forms a flexible contact interface wherein the flexibility of the stylet contact interface reduces damage to the reservoir or the catheter and where the stylet is removable from the catheter to permit fluid delivery; and wherein the strain relief member increases a resistance to bending of the catheter over the length upon removal of the stylet and maintains a bend radius above a critical radius when the force displaces the catheter from a neutral position of the catheter relative to the wall.

In another variation, the methods and/or devices can include the concept described above comprising the medical device and stylet with stylet tip as described herein.

Another variation of a device can include a fluid delivery system for positioning a medical device in a patient and delivering a fluid to a reservoir enclosed in the device. For example, such a system can include a catheter comprising a fill end, a delivery end, and a mid-portion, wherein said delivery end is configured to be inserted through a wall of the reservoir at a reservoir wall interface; a strain relief member coupled to a length of the delivery end of the catheter such that the strain relief member increases a stiffness of the length to greater than a stiffness of the mid-portion of the catheter, which reduces kinking at the length when a force is applied on the catheter; and wherein the strain relief increases a resistance to bending of the catheter over the length and maintains a bend radius above a critical radius when the force displaces the catheter from a neutral position of the catheter relative to the wall and wherein the strain relief provides a transition between a stiffness of the reservoir wall interface and the stiffness of the mid-portion of the catheter.

In another variation, the methods and devices can comprise a fluid delivery system for placing a medical device in a patient and delivering a fluid to an enclosed reservoir in the device. An example of such a system includes a flexible catheter comprising a fill end and a delivery end, wherein said delivery end is configured to be inserted through a wall of the reservoir; a stylet designed to fit within a lumen of the catheter, the stylet comprising an operator's end and a far end; a stylet tip located at a far end of the stylet, wherein a flexibility of the stylet tip is greater than a remainder of the stylet such that the stylet tip forms a flexible contact interface wherein the flexibility of the stylet contact interface reduces damage to the reservoir or the catheter and where the stylet is removable from the catheter to permit fluid delivery; and wherein the stylet is inserted through the lumen of the catheter from the fill end to advance the device within the patient prior to delivery of the fluid, the stylet being removed before fluid delivery initiation.

In one example the system, the length starts at or inside the wall and extends towards the fill end. In an additional variation, the strain relief increases a stiffness of the catheter substantially uniformly over a length of the strain relief. For example, the length of the strain relief can be configured to permit the length of the catheter to flex without kinking over the length of the catheter.

In another variation, the strain relief includes a covering of a flexible material. For example, the flexible material can be an ink, a polymer tube, and/or a combination thereof.

In another variation, the strain relief provides a tapered decrease in the stiffness of the catheter from a higher value to a lower value over the length of the strain relief, with the higher value disposed towards the delivery end of the catheter. In one example, the length of the strain relief is determined by design to maintain the catheter's bend radius above a critical radius. Alternatively, or in combination, the stiffness of the strain-relieved catheter at the wall is comparable to a maximum stiffness of the wall. In another example, the stiffness of the strain-relieved catheter at the end of the length of the strain relief is substantially equal to the stiffness of the catheter without the strain relief.

The strain relief can be created with a tapered stiffness coating of flexible material. For example, the tapered stiffness can be created by a tapered section of the flexible material. The tapered section of the flexible material can comprise a series of stepped sections. For example, the tapered stiffness can be created by a binary patterning of the flexible material.

In an additional variation, the stylet tip is a flexible extension to the stylet. For instance, the flexible extension can be a length of polymer tubing. The polymer tubing can be a thermoplastic or heat shrinkable tubing. In one variation, the length of the tubing that extends beyond the tip of the stylet is preferably between 5 and 50 millimeters and more preferably between 20 and 30 millimeters. Alternatively, or in addition, the length of the tubing that covers the distal end of the stylet is designed to hold the tubing on the stylet by friction.

The above and other features of the invention including various novel details of construction and combinations of parts, and other advantages, will now be more particularly described with reference to the accompanying drawings and claims. It will be understood that the particular methods and devices conveying the inventive features are shown by way of illustration and not as a limitation of the invention. The principles and features of this invention may be employed in various and numerous embodiments without departing from the scope of the invention.

BRIEF DESCRIPTION OF THE DRAWINGS

The foregoing and other objects, features and advantages of the methods, devices, and systems described are shown in the following description in conjunction with the accompanying drawings, in which reference characters refer to the same parts throughout the different views. The drawings are not necessarily to scale; emphasis has instead been placed upon illustrating the principles of the invention.

FIG. 6A illustrates a cross-section view of an embodiment of a tapered strain relief.

FIG. 6B illustrates a cross-section view of a stepped embodiment of the tapered strain relief of FIG. 6A.

FIG. 8 is a table of strain relief performance.

DETAILED DESCRIPTION OF THE INVENTION

In describing the methods and devices of the present invention, it is to be understood the variations are not limited to the variations disclosed herein since various changes or modifications can be made to the methods, devices, and systems. In addition, equivalents can be substituted as needed without exceeding the scope of the invention disclosure. Those of skill in the art, upon reading this disclosure, will understand that each of the individual embodiments disclosed herein includes discrete components and features that can be readily separated from or combined with the features of any of the additionally described variations without departing from the scope of the present disclosure. In addition, many modifications may be made to adapt a particular situation, material, composition of matter, process, process act(s) or step(s) to the objective(s), spirit or scope of the present invention. All such modifications are intended to be within the scope of the claims made herein. Especially, any claim can be combined with another claimed unless the claim explicitly prohibits such a disclosure.

The following illustrations are examples of the invention described herein. It is contemplated that combinations of aspects of specific embodiments or combinations of the specific embodiments themselves are within the scope of this disclosure. The methods, devices, and systems described herein are discussed as being used with a gastric balloon device for convenience for illustrative purposes only. It is intended that the devices, methods, and systems of the present disclosure can be used with other devices where fluid is delivered into/out of the device. For example, such devices can include fluid-inflatable devices that are deployed and inflated with a fluid after insertion into the body. Further, the methods, devices, and systems described herein can be used in devices in which a flexible catheter passes through a more rigid barrier.

Figure 1:
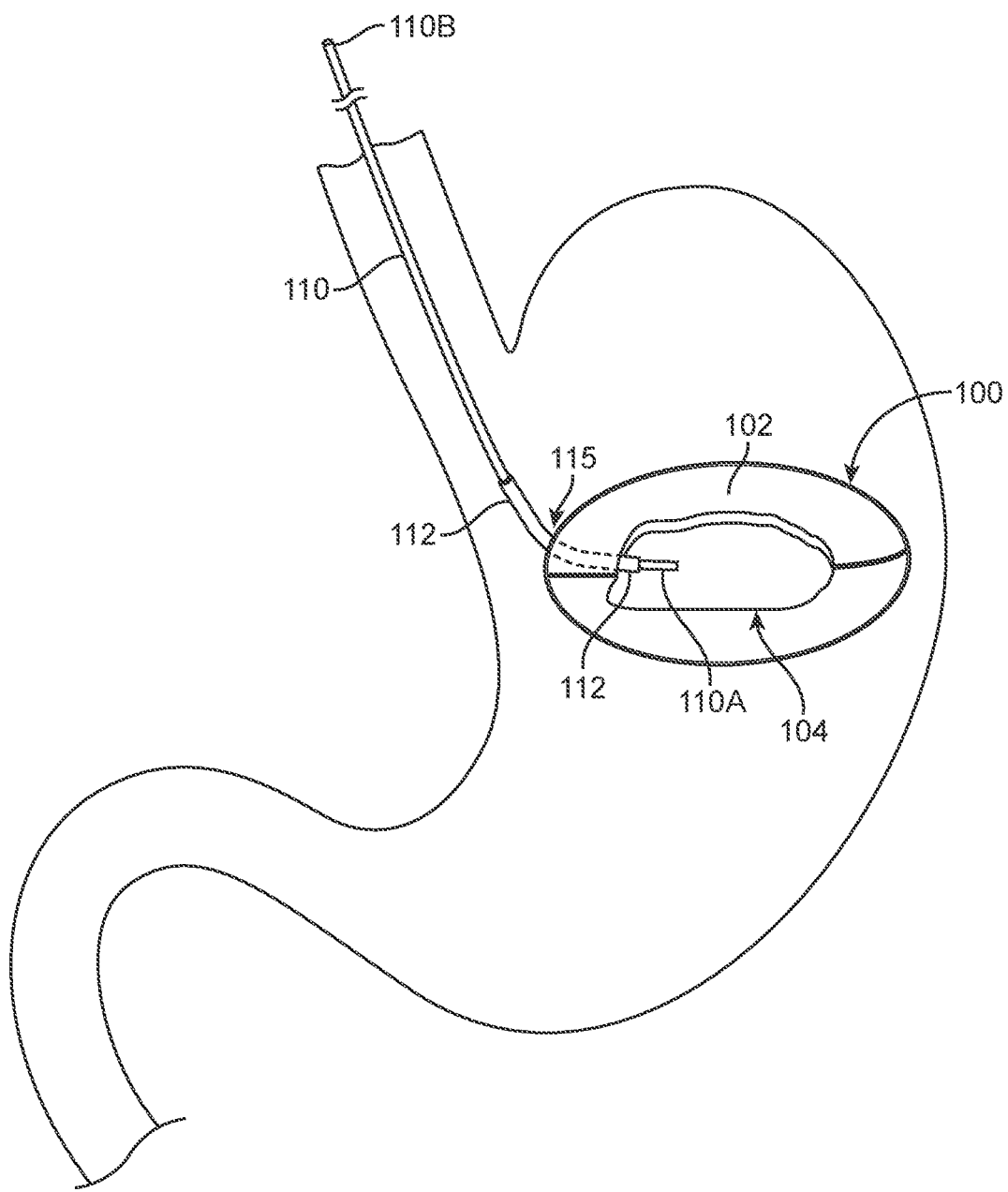
FIG. 1 illustrates a gastric balloon device.

FIG. 1 is an illustration of a balloon device 100, specifically a gastric balloon for weight reduction, positioned in a patient's stomach. Again, the present disclosure includes the concepts described herein for use with other balloon devices in a wide variety of medical procedures, some of which shown in Table 1. Balloon devices generally comprise two states: a pre-deployment or uninflated configuration and a deployed, inflated, or active configuration. Generally, a fluid delivered through a tube 110, inflates the device 100, where the tube 110 can also be referred to as a catheter or conduit. The tube may pass through an opening 115 in wall 102 of the balloon device 100. Alternatively, as shown, the tube 110 can be coupled to a fluid path 112, which fluidly connects the exterior and the interior of the balloon device. The end of catheter 110 that delivers the fluid to the interior reservoir of the balloon is the delivery end 110A while the opposite end is the fill end 110B, into which fluid is introduced.

In many balloon devices 100, a wall 102 of the balloon is fabricated from a thin film material such as, for example, polyurethane. In some variations, tube 110 comprises a balloon, or delivery, end 110A that extends through fluid path 112 into a central enclosed space or reservoir 104 of device 100. Conduit 110 is removed from the device once inflation is completed. When catheter 110 is removed, fluid path 112 must be sealed to prevent the inflation fluid from leaking out through fluid path 112 from reservoir 104. Again, in some variations, a fill valve, not illustrated, seals the device 100. In some variations the fill valve or the fluid path 112 acts to constrain tube 110 to pass through wall 102 at a fixed angle relative to the local normal to the wall. In some variations the angle is 90 degrees (that is, tube 110 is normal to wall 102) while in other variations tube 110 may pass through wall 102 at a shallower angle, even approaching 0 degrees.

TABLE 1

Balloon Device Uses

| Medical Specialty | Procedure |
| --- | --- |
| Carotid & Neurovascular | Angioplasty, Occlusion |
| ENT | Sinuplasty |
| Cardiovascular | Angioplasty, Stent Delivery, IVUS, Vulnerable Plaque detection |
| Structural Heart | Valvuloplasty, Heart Valve sizing and dilation, Aortic pump & Cardioplegia, Occlusion, Sizing |
| Electrophysiology | Cryoablation |
| EVAR | Sizing, placement, tacking balloons, endovascular stent graft delivery |
| GI | Esophageal & biliary dilation, GI access & stent placement |
| Venous & AV access | High pressure balloons |
| Iliac | PTA balloons |
| SFA | Long PTA balloons |
| Popliteal, infrapopliteal, pedal, plantar | low profile balloons |
| MI Orthopaedic | Kyphoplasty |
| Peripheral Vascular | Renal, thrombus aspiration, stent graft delivery |
| Cosmetic Surgery | Breast Augmentation |

Figure 2A:
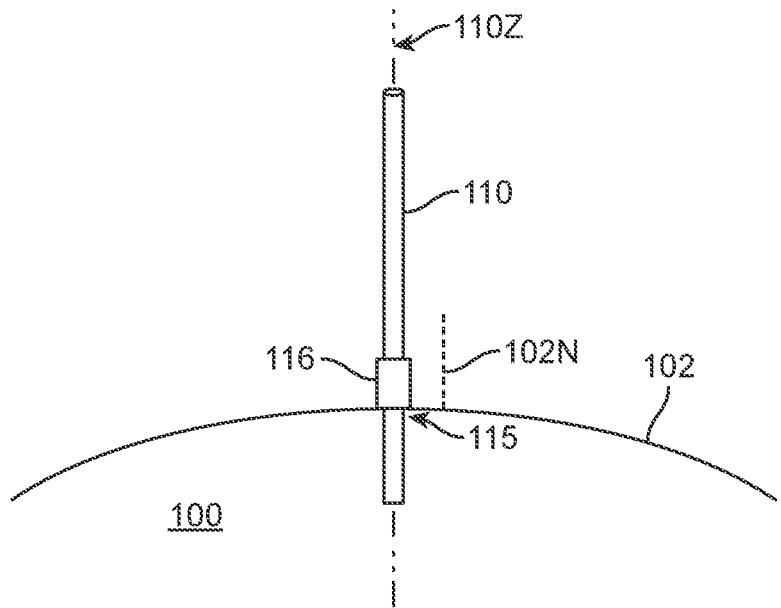
FIGS. 2A and 2B illustrate a fluid delivery catheter connected to an unfilled balloon.

Prior to the balloon being filled, thin film wall 102 is flexible. When tube 110 is constrained to pass through wall 102 at a fixed angle, any movement of tube 110 affects, bends, or distorts wall 102 such that the angle at which tube 110 passes through wall 102 is constant. FIG. 2A illustrates the nominal configuration of a tube 110 passing through an opening 115 in a section of wall 102 of thin film material that defines balloon device 100. Tube 110 passes through a constraining element 116, which may be, for example, a fluid path or fill valve. In this illustration tube 110 has an axis 110Z, which is constrained by element 116 to be parallel to the surface normal 102N of wall 102.

Figure 2B:
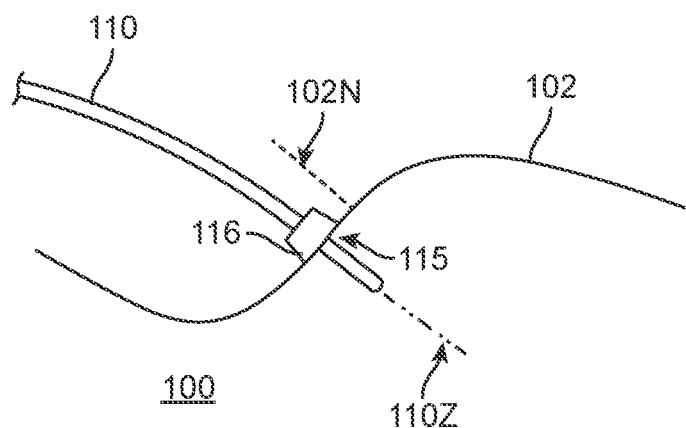
Figure 3:
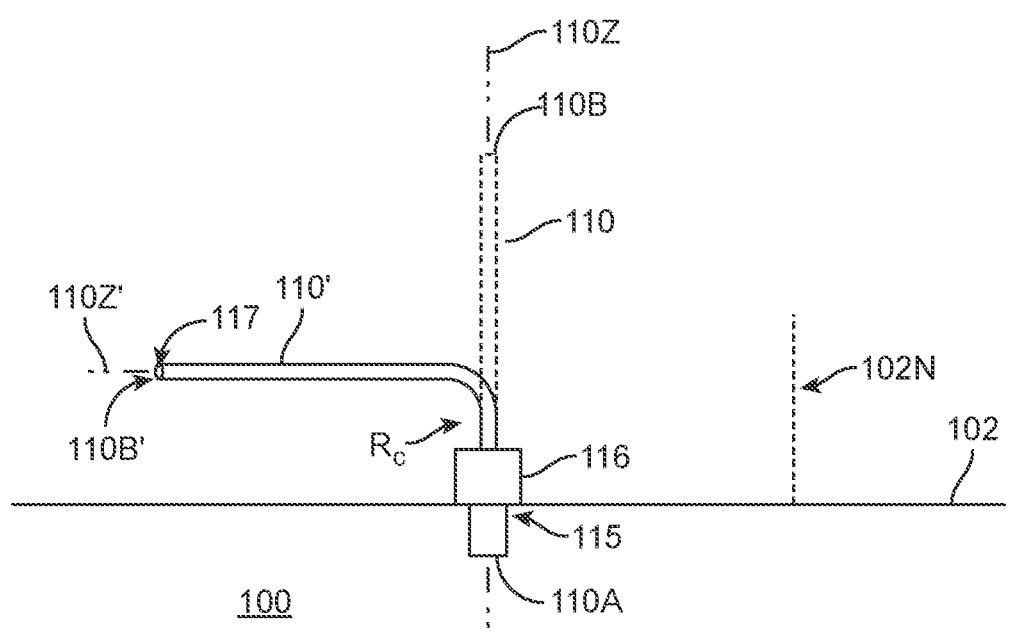
FIG. 3 illustrates a fluid delivery catheter connected to a filled balloon.

As further illustrated in FIG. 2B, when there is no significant pressure within device 100 wall 102 shape is distorted when tube 110 is pulled to one side so that the parallel relationship between tube axis 110Z and wall normal 102N is maintained. On the other hand, as balloon device 100 is filled with a fluid the internal pressure in device 100 increases and wall 102 experiences increasing tension. In turn, the increasing tension stiffens wall 102 making it resistant to distortion. In particular, after balloon 100 is inflated close to capacity, wall 102 is placed in tension and becomes relatively stiff. FIG. 3 illustrates that tensioned wall 102 has limited ability to tilt locally to maintain the surface normal 102N parallel to the catheter axis 110Z. Instead, catheter 110' must bend to when the fill end 110B' is deflected to the side. There is a limit to how far catheter 110' may be pulled to the side before the decreasing radius of the curvature at the bend point reaches a critical radius, $R_C$. Any additional pull on the catheter causes the inner side of the curved catheter to fold or kink, shown in tube 110'. This folding reduces the fluid flow through the catheter and may weaken tubular wall 117 of the catheter. For highly flexible tube structures such as the catheter, $R_C$ is small, and kinking occurs very close to the constraining element, illustrated as collar 116, between the tube 110 and the much less flexible balloon wall 102, that is, kinking in a tube occurs where there is a sharp discontinuity in the effective stiffness of the tube. This discontinuity can be eliminated by an angular strain-relief component 10, as shown in FIG. 3.

In some instances, the fill valve and/or the fluid path 112 may be designed to include angular strain relief. Angular strain relief is a means of reinforcing a generally flexible, linear component—a wire or tube—that is attached to a stiff and somewhat fixed attachment point to prevent the linear component from being damaged or kinked by a lateral force, that is, being pulled by a force directed perpendicular to the linear component's axis.

In the case of a flexible tube like a catheter, the kinking that occurs because of the lateral force is well understood. As explained in *Mechanical Properties of Catheters* (Acta Radiologica: Diagnosis, 4:sup260, 11-22) incorporated by reference herein, a straight catheter held fixed at one end and subjected to a force perpendicular to its axis takes on a curvature with a radius $$R = \frac{EI_o}{M} \quad (1)$$

where

E is the modulus of elasticity of the catheter material, $I_o$ is the moment of inertia of the catheter with respect to its normal axis, and M is the bending moment (that is, force applied to bend) applied to the catheter.

For a fixed M, the radius can be increased by changing the material to one with a higher modulus of elasticity (that is, a fixed applied force will bend a stiffer material less) or changing the geometry of the catheter to increase the moment of inertia. For a tube, $$I_o = \frac{\pi(D^4 - d^4)}{64}, \quad (2)$$

where D is the outer diameter of the catheter and d is its inner diameter. Clearly, the radius R depends strongly on the wall thickness (D−d)/2. For a catheter with a fixed inner diameter the wall thickness increases linearly with outer diameter D.

Appendix A further explains the critical radius. The critical radius, $R_C$, is the smallest radius into which the catheter can be bent before it kinks (reducing or stopping fluid flow through the catheter). From the appendix, $$R_C = K(D^2/(D-d)), \quad (3)$$

where the scaling factor K is nearly constant for all catheter materials of interest. As a general rule it is desirable to have a small critical radius, which allows one to bend a catheter sharply without kinking. In any particular use, the catheter inner and outer diameter are selected to achieve the required $R_C$, with the critical radius generally decreasing with decreasing outer diameter (the inner diameter is typically fixed to achieve the desired fluid flow at a fixed pressure).

As described above, a tube will kink as the bending radius decreases to become equal to the critical radius. While it is possible to stiffen the catheter by increasing the outer diameter of the entire catheter to make it harder to reach the critical radius, it is usually more desirable to maintain high flexibility over most of the length of the catheter to facilitate placement through a tortuous path that must be navigated between outside the body and the device's ultimate operational location. Thus, the purpose of an angular strain relief is to prevent the catheter's bending radius from reaching the critical radius in the immediate vicinity of the device, where the catheter is angularly constrained by the connection to the device wall, while maintaining the flexibility of the majority of the length of the catheter.

An angular strain relief acts to reduce the inherent discontinuity between the stiff constraining element and the flexible catheter. The strain relief, in one variation, is designed to provide a transition zone along the catheter where the zone has a continuously varying stiffness (or, equivalently a continuously varying critical radius) such that it matches the constraining element at one end and the inherent properties of the catheter at the other. By eliminating any discontinuity along the catheter, the strain relief reduces the potential for kinking. In another variation the continuously varying strain relief can be approximated by a uniform strain relief or a stepped strain relief, each of which reduce the magnitude of the discontinuity between the stiff constraining element and the flexible catheter.

Figure 4:
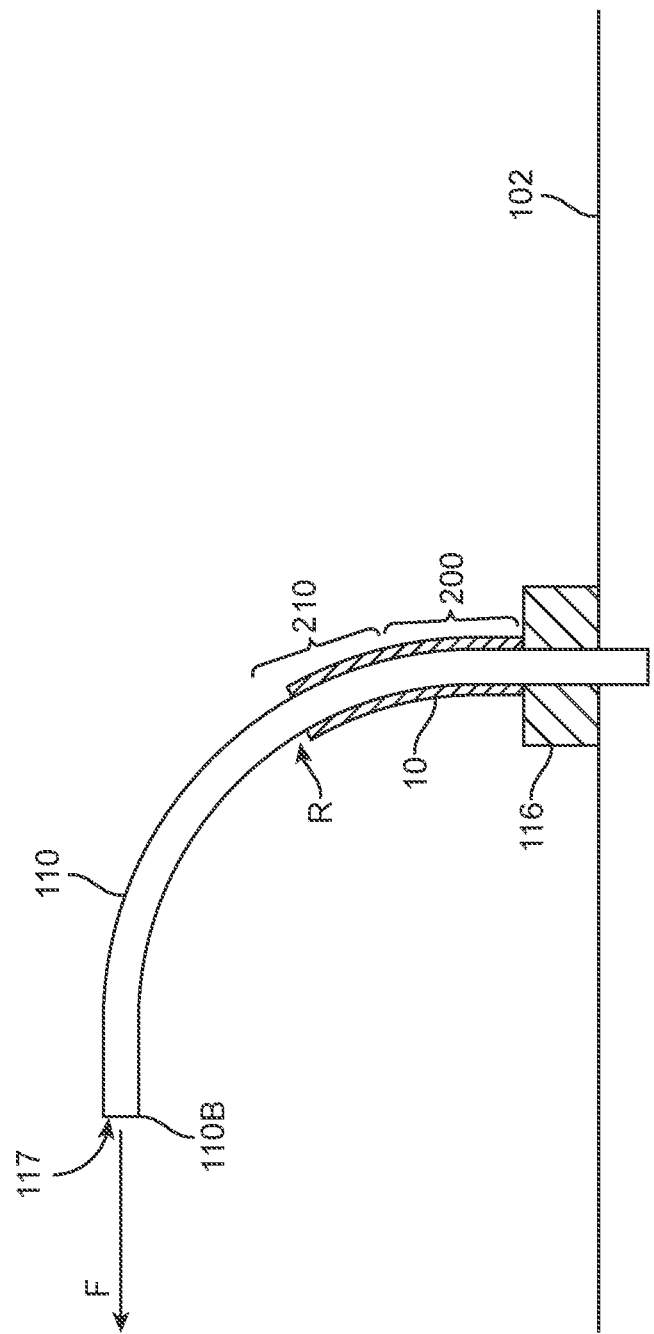
FIG. 4 is a cross-section view of a strain relieved catheter being displaced.

FIG. 4 illustrates a cross-section of a catheter with one embodiment of a strain-relief component 10. Strain relief component 10 is designed to be stiff enough to keep the bending radius in the interface region 200 near the connection to the device wall above the critical radius, yet flexible enough to bend towards the laterally displaced catheter to reduce the bending moment M felt by the portion of the catheter that extends beyond the end of the strain relief. In the illustrated embodiment, strain relief component 10 is a uniform coating or sleeve that covers catheter's 110 outer surface, changing either or both the effective stiffness of the catheter material or the outer diameter of catheter 110 in region 200. FIG. 4 illustrates catheter 110 after it has been pulled to the side by fill end 110B. Catheter 110 is a flexible, hollow, thin-walled tube. It is surrounded by strain relief 10, which is also a flexible tube-like element. As illustrated, the strain relieved catheter has an increased bend radius in the interface region 200 generally and catheter 110 bends in the direction of the applied force F, as indicated by the arrow, significantly reducing the amount by which the catheter itself must bend in a terminus region 210 where strain relief 10 ends, thus increasing the bending radius, R, above the critical radius $R_C$.

Figure 5:
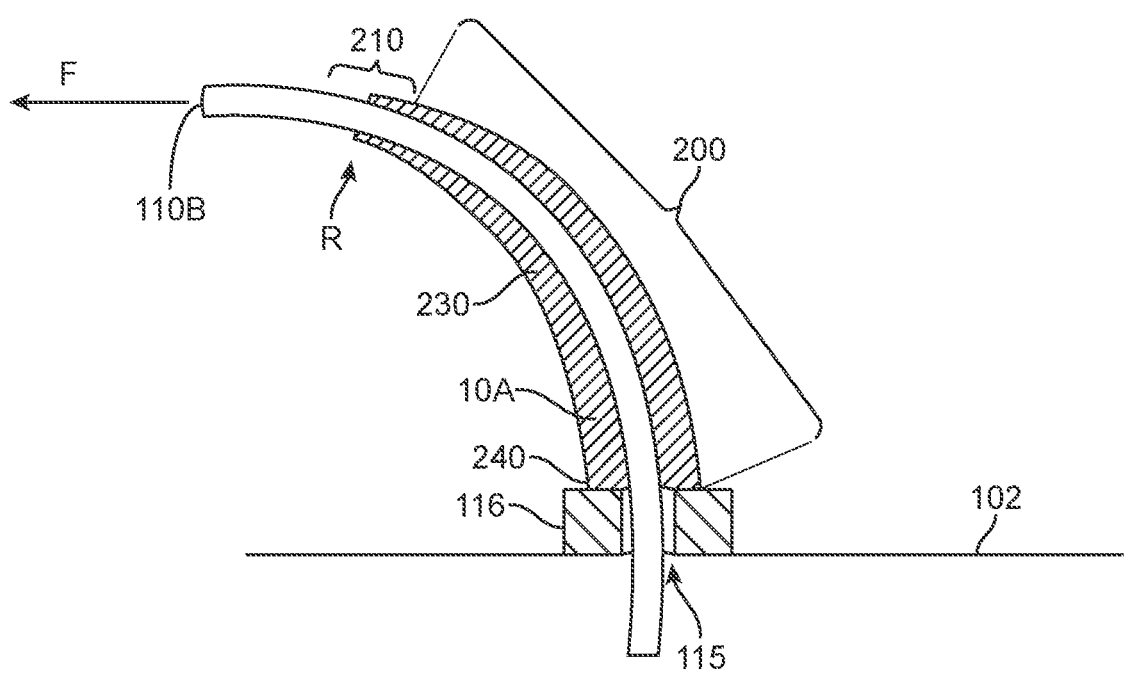
FIG. 5 illustrates a cross-section view of one embodiment of a tapered strain relief when the catheter is displaced.

In another embodiment, illustrated in cross-section in FIG. 5, the walls 230 of a tubular strain relief 10A are tapered. This taper creates a continuously varying stiffness and thus bending radius of the catheter in region 200 that corresponds to the variation in wall thickness. Thus, at the constrained end 240 of strain relief 10A the relief 10A is designed to be about as stiff as wall 102 to which it is attached, significantly increasing the bending radius for a given lateral force F near collar 116. Equivalently, in the terminus region 210 of strain relief 10A the added stiffness of the strain relief is almost zero and the strain relief itself has bent to point toward the fill end 110B of the offset catheter, meaning there is no discontinuity in the effective stiffness of tube 110 in the terminus region 210 where the strain relief ends. By providing a continuum of stiffness between the constrained end 240 and the terminus region 210 the strain relief eliminates the catheter bend radius from ever reaching $R_C$.

A tapered-wall embodiment of strain relief 10 can be approximated by a stepped-wall embodiment 10B. For the purposes of comparison, FIG. 6 is divided into a right-side figure, FIG. 6A, which illustrates the continuously tapered strain relief 10A of FIG. 5 while the left side figure, FIG. 6B, illustrates a stepped wall embodiment 10B. As its name suggests, a stepped-wall strain relief 10B comprises a wall thickness that varies from thick to thin in stepped manner, wherein the steps 242 can be fabricated in a variety of ways. First, for example, a single, thick strain relief can be cut away to create the desired stepped strain relief. In a second example, the steps can be formed by adding multiple thin layers of wall material, each successively shorter than the preceding layer. In a third fabrication approach the step function can be molded or cast in one piece.

Figure 7A:
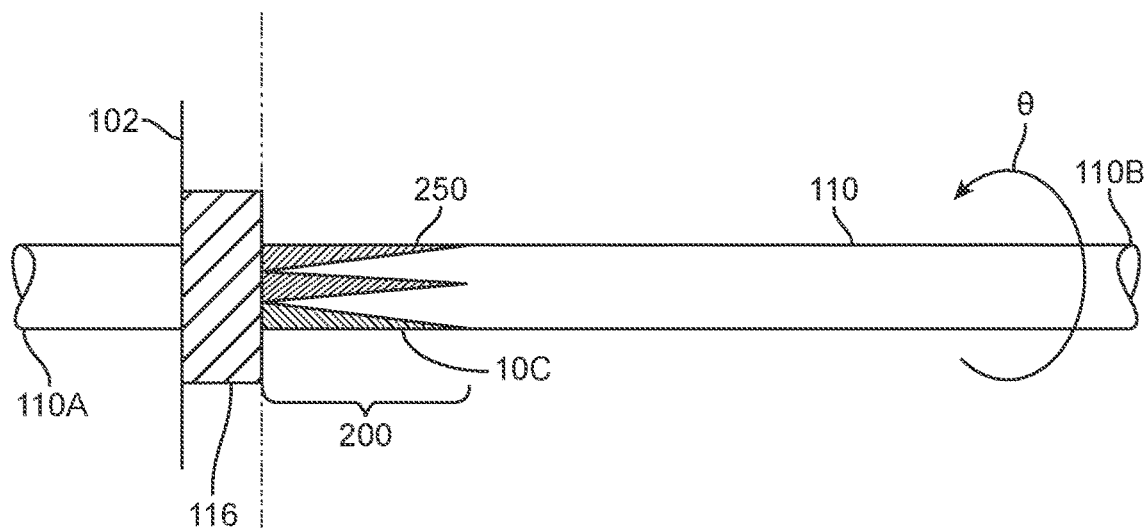
FIG. 7A is a side view of a spatially modulated strain relief.
Figure 7B:
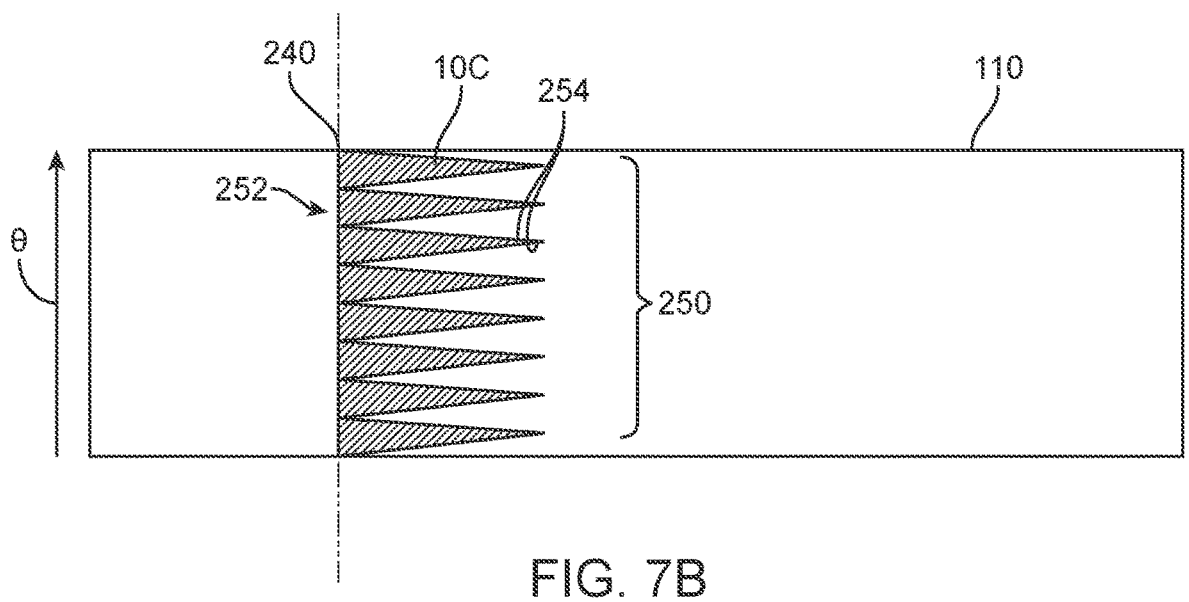
FIG. 7B illustrates the spatial modulation pattern of the strain relief of FIG. 7A unwrapped for clarity.

In another embodiment, a tapered strain relief with nontapered walls may be created by patterning, or spatially modulating, the strain relief's wall. FIG. 7A illustrates a side view of catheter 110 with one variation of a spatially modulated strain relief 10C. As shown in the illustration, spatially modulated strain relief 10C comprises a pattern 250 around the exterior of catheter 110. This embodiment, pattern 250, is a zig-zag pattern more clearly seen in FIG. 7B, which shows strain relief 10C unwrapped from catheter 110. That is, the figure illustrates the varying length of the spatially modulated strain relief wall (as measured from constrained end 240) as a function of angle, θ, around catheter 110.

In the illustrated variation, the spatial modulation is an elongated zig-zag pattern, which can also be described as a series of triangular shapes. Each triangular shape in this example is an isosceles triangle with a narrow base 252 and two elongated sides 254. The width of the base has been selected to be less than one half of the circumference of the catheter and also a fraction of the circumference. That is, there are a whole number, greater or equal to 2, of triangular shapes around the circumference. This pattern is illustrative of desirable properties of a pattern for a spatially modulated strain relief. First, the wall of the strain relief itself does not have a tapered thickness so it can be fabricated from a simple tube of material. Second, the modulation function comprises only straight lines which are easier to create than curved lines. Third, the modulation pattern repeats multiple times around the circumference of the catheter so there is little or no angular variation in the stiffness of the strain relief around the circumference of the catheter.

In some variations, a spatially modulated strain relief is a separate component that surrounds the catheter or tube. In another variation, the strain relief is printed directly onto the catheter. The thickness and composition of the ink used in this printing process increases the stiffness of the catheter just as a layer of tubing or molded overcoat would do. For small diameter catheters, cutting or otherwise fabricating the modulated features in a stand-alone, spatially modulated strain relief is less preferred to simply printing the same features directly on the tubing. Conveniently, adding a printed strain relief can be accomplished with little or no extra expense if the catheter is already being printed with other markings. In some variations these markings are used to estimate the location of the delivery end 110A of the catheter along the gastro-intestinal tract.

FIG. 8 is a table of experimental data illustrating the effectiveness of a spatially modulated strain relief to inhibit kinking. Testing was performed in a test fixture in which the test object (catheter) was held in a rigid channel with the free end pointing upwards. The free end of the catheter was allowed to drape over the edge of the table. Weights of increasing mass were loaded onto the free end in controlled, timed intervals. The mass at which kinking occurred was determined by visual observation of the shape of the catheter at the catheter/channel interface. As shown in the table, the weight required to induce a kink in the strain-relieved catheters was approximately 2.5 times greater than the weight required to kink an unmodified catheter.

Increased Safety Stylet

In some situations, a fluid delivery system further comprises a stylet for assisting in placement of a medical device. A stylet is, essentially, a thin and relatively stiff, wire-like object that is used to push the medical device towards its intended placement location. In some situations, as with a gastric balloon medical device, the device is delicate and can be damaged if the thin wire tip of the stylet pushes too hard against the device. In some instances, the stylet may not only puncture the device but may pass entirely through the device and injure the patient.

Figure 9:
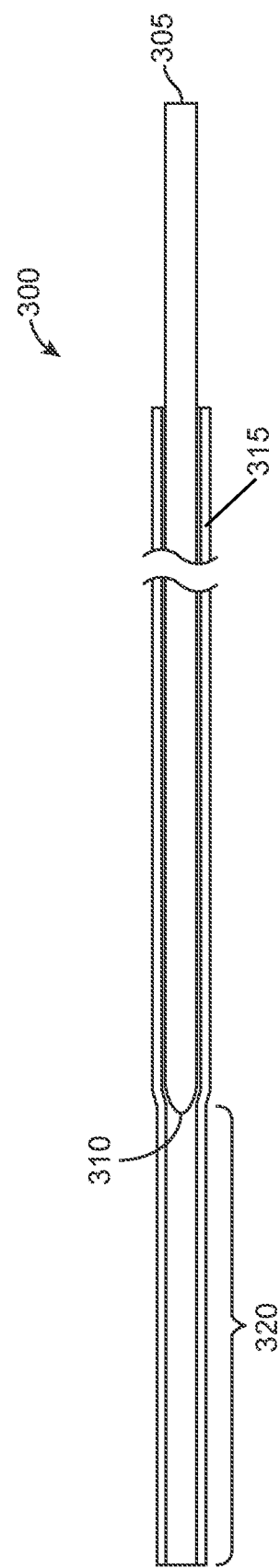
FIG. 9 illustrates an embodiment of the increased safety stylet.

FIG. 9 illustrates an embodiment of an increased safety stylet. In use, a stylet is inserted into fill end 110B of catheter 110 and fed into the catheter until its distal or push end 310 reaches the device at the end of the catheter. In some situations, such as when a medical device is to be swallowed by the patient, the patient may initially attempt to swallow the device unassisted prior to stylet insertion, with the stylet being inserted to assist only if the patient is unable to swallow the device unassisted. With the stylet in place inside the catheter, the administering agent can push the device to move it beyond the upper esophageal sphincter (UES), which may also been referred to as the inferior pharyngeal sphincter because it is located at the lower end of pharynx and guards the entrance into the esophagus where the patient's gag reflex has previous caused the patient to reject the device.

The variation of a safety stylet 300 illustrated in FIG. 9 has a compliant tip 320 disposed on push end 310 to reduce the incidence of device puncture or patient injury. In this variation, compliant tip 320 comprises a length of polymer tubing 315 attached to the push end 310 of stylet wire 305. Polymer tubing 315 may be polytetrafluoroethylene (PTFE), commonly called "heat-shrink" tubing, or any similar polymer such as polyetheretherketone (PEEK) or fluorinatedethylenepropylene (FEP). The use of a heat-shrinkable tubing provides a convenient means of attaching tubing 315 to stylet 300. In some embodiments tubing 315 extends a significant length along stylet wire 305

In the embodiment illustrated in FIG. 9 stylet 300 comprises an approximately 36-inch-long, 24 mil diameter stainless steel wire 305. Push end 310 of wire 305 is preferably rounded to reduce tearing of compliant tip 320. A length of heat-shrink tubing 315 having an unshrunk inner diameter slightly greater than the 24 mil diameter of wire 305 is positioned over the wire, leaving a pre-determined length of tubing, in this exemplary embodiment approximately 0.25 inches, protruding past push end 310 to serve as compliant tip 320. In this embodiment the length of heat shrink tubing has been selected to cover substantially the entire length of wire 305 to ensure the stylet is smooth and lubricious.

After positioning on wire 305, the entire length of tubing 315 is heated above the shrinkage temperature. A smaller diameter mandrel wire may be inserted into protruding tip 320. After heat-shrinking, tube 315 is tightly attached to wire 305 but, due to its smaller diameter, not tightly attached to the mandrel wire, if used. The mandrel wire is merely tooling and is removed after heat-shrinking.

We claim:

1. A medical device for positioning in a patient, the medical device comprising:
   a reservoir enclosed in the medical device and configured to receive a fluid;
   a catheter comprising a fill end and a delivery end, wherein the delivery end is configured to be fluidly coupled to the reservoir;

a strain relief member supporting a portion of a length of the catheter at the delivery end, where the strain relief member increases a stiffness of the length to reduce kinking at the length when a force is applied on the catheter that deflects the catheter relative to the medical device;

a stylet configured to fit within a lumen of the catheter;

a stylet tip located at a far portion of the stylet, wherein a flexibility of the stylet tip is greater than a remainder of the stylet such that the stylet tip forms a flexible contact interface wherein the flexibility of the flexible contact interface reduces damage to the reservoir or the catheter and where the stylet is removable from the catheter to permit fluid delivery; and wherein the strain relief member increases a resistance to bending of the catheter over the length upon removal of the stylet and maintains a bend radius above a critical radius when the force displaces the catheter from a neutral position of the catheter relative to a wall of the reservoir.

2. The medical device of claim 1 where the length starts at or inside the wall and extends towards the fill end.

3. The medical device of claim 2 where the strain relief member increases a stiffness of the catheter substantially uniformly over a length of the strain relief member.

4. The medical device of claim 3 where the length of the strain relief member is configured to permit the length of the catheter to flex without kinking over the length of the catheter.

5. The medical device of claim 3 where the strain relief member includes a covering of a flexible material.

6. The medical device of claim 5 where the flexible material is an ink or a polymer tube.

7. The medical device of claim 1 where the strain relief member provides a tapered decrease in the stiffness of the catheter from a higher value to a lower value over the length of the strain relief member, with the higher value disposed towards the delivery end of the catheter.

8. The medical device of claim 7 where the length of the strain relief member is determined by design to maintain a bend radius of the catheter above the critical radius.

9. The medical device of claim 7 where the stiffness of the catheter at the strain relief member is comparable to a maximum stiffness of the wall.

10. The medical device of claim 7 where the stiffness of the catheter at an end of the length of the strain relief member is substantially equal to the stiffness of the catheter without the strain relief member.

11. The medical device of claim 7 where the strain relief member is created with a tapered stiffness coating of flexible material.

12. The medical device of claim 11 where the tapered stiffness coating is created by a tapered section of the flexible material.

13. The medical device of claim 12 where the tapered section of the flexible material comprises a series of stepped sections.

14. The medical device of claim 12 where the tapered stiffness coating is created by a binary patterning of the flexible material.

15. The medical device of claim 1 where the stylet tip is a flexible extension to the stylet.

16. The medical device of claim 15 where the flexible extension is a length of polymer tubing.

17. The medical device of claim 16 where the polymer tubing is a thermoplastic or heat shrinkable tubing.

18. The medical device of claim 17 where the length of the polymer tubing that extends beyond the stylet tip is preferably between 5 and 50 millimeters.

19. The medical device of claim 18 where the length of the polymer tubing that covers a distal end of the stylet is designed to hold the polymer tubing on the stylet by friction.

20. A fluid delivery system for positioning a medical device in a patient and delivering a fluid to a reservoir enclosed in the medical device, the fluid delivery system comprising:

a catheter comprising a fill end, a delivery end, and a mid-portion, wherein said delivery end is configured to be inserted through a wall of the reservoir at a reservoir wall interface;

a strain relief member coupled to a length of the delivery end of the catheter such that the strain relief member increases a stiffness of the length to greater than a stiffness of the mid-portion of the catheter, which reduces kinking at the length when a force is applied on the catheter; and wherein the strain relief member increases a resistance to bending of the catheter over the length and maintains a bend radius above a critical radius when the force displaces the catheter from a neutral position of the catheter relative to the wall and wherein the strain relief member provides a transition between a stiffness of the reservoir wall interface and the stiffness of the mid-portion of the catheter.

* * * * *